US011447936B2

(12) United States Patent
Takami et al.

(10) Patent No.: US 11,447,936 B2
(45) Date of Patent: Sep. 20, 2022

(54) OIL DIAGNOSIS SYSTEM

(71) Applicant: HITACHI CONSTRUCTION MACHINERY CO., LTD., Tokyo (JP)

(72) Inventors: Hiroki Takami, Ushiku (JP); Akira Kurasako, Tsuchiura (JP); Kotaro Ogura, Katsushika-ku (JP); Hideki Akita, Tsuchiura (JP); Hiroshi Onose, Mito (JP); Yoshiya Hamamachi, Toride (JP)

(73) Assignee: HITACHI CONSTRUCTION MACHINERY CO., LTD., Tokyo (JP)

( * ) Notice: Subject to any disclaimer, the term of this patent is extended or adjusted under 35 U.S.C. 154(b) by 416 days.

(21) Appl. No.: 16/492,229

(22) PCT Filed: Nov. 8, 2017

(86) PCT No.: PCT/JP2017/040273
§ 371 (c)(1),
(2) Date: Sep. 9, 2019

(87) PCT Pub. No.: WO2019/021502
PCT Pub. Date: Jan. 31, 2019

(65) Prior Publication Data
US 2020/0325657 A1    Oct. 15, 2020

(30) Foreign Application Priority Data

Jul. 28, 2017 (JP) .............................. JP2017-147210

(51) Int. Cl.
*F01M 11/10* (2006.01)
*E02F 9/26* (2006.01)
(Continued)

(52) U.S. Cl.
CPC .............. *E02F 9/267* (2013.01); *F16N 29/04* (2013.01); *G01N 11/00* (2013.01);
(Continued)

(58) Field of Classification Search
CPC .......... F01M 11/10; F01M 2011/1413; F01M 2011/148; F16N 2250/36; F16N 2200/00;
(Continued)

(56) References Cited

U.S. PATENT DOCUMENTS 6,151,956 A    11/2000 Takahashi et al.
2004/0128107 A1    7/2004 Ryu et al.
(Continued)

FOREIGN PATENT DOCUMENTS

JP    09-127067 A    5/1997
JP    11-118774 A    4/1999
(Continued)

OTHER PUBLICATIONS

International Preliminary Report on Patentability received in corresponding International Application No. PCT/JP2017/040273 dated Feb. 6, 2020.

(Continued)

*Primary Examiner* — Long T Tran
(74) *Attorney, Agent, or Firm* — Mattingly & Malur, PC

(57) ABSTRACT

A computer for a manufacturer includes: a storage device storing amount-of-change determination values specified for respective amount-of-change indexes indicative of tendencies of temporal changes in pieces of sensor data A, B, and C, about a plurality of oil properties including a viscosity, a density, and a dielectric constant of oil; an abnormality determining section determining abnormality of the oil on the basis of the pieces of sensor data A, B, and C about the plurality of oil properties and abnormality determination values SAh, SAl, SBh, and SCh prescribed for the respective pieces of sensor data A, B, and C about the plurality of oil properties; a cause identifying section identifying, when the abnormality determining section determines the oil to be abnormal, the cause of the abnormality on the basis of the (Continued)

type of the oil property determined to be abnormal and the amount-of-change determination value of the oil property.

7 Claims, 10 Drawing Sheets

(51) Int. Cl.
*F16N 29/04* (2006.01)
*G01N 11/00* (2006.01)
*G01N 33/28* (2006.01)
*G05B 23/02* (2006.01)

(52) U.S. Cl.
CPC ..... *G01N 33/2888* (2013.01); *G05B 23/0259* (2013.01); *F16N 2200/00* (2013.01); *F16N 2200/04* (2013.01); *F16N 2200/12* (2013.01); *F16N 2200/20* (2013.01); *F16N 2210/04* (2013.01); *F16N 2250/36* (2013.01); *G01N 2011/0066* (2013.01)

(58) Field of Classification Search
CPC ............. F16N 2200/04; F16N 2200/12; F16N 2210/04; F16N 2250/30; F16N 2260/18; F16N 29/04
See application file for complete search history.

(56) References Cited

U.S. PATENT DOCUMENTS

| | | |
|---|---|---|
| 2009/0315574 A1 | 12/2009 | Akiyama et al. |
| 2012/0229151 A1 | 9/2012 | Katafuchi |
| 2017/0081997 A1* | 3/2017 | Potyrailo ........... G01N 33/2888 |
| 2017/0284068 A1* | 10/2017 | Nakamura ............. G01N 33/30 |
| 2018/0231518 A1* | 8/2018 | Vaidya ..................... F01M 1/02 |
| 2018/0306616 A1* | 10/2018 | Gillette, II ............... G01F 1/56 |
| 2018/0308294 A1* | 10/2018 | Abuelsaad ............ G07C 5/008 |
| 2020/0309641 A1* | 10/2020 | Balboni ............. G01M 17/007 |

FOREIGN PATENT DOCUMENTS

| | | |
|---|---|---|
| JP | 2004-211884 A | 7/2004 |
| JP | 2007-100712 A | 4/2007 |
| JP | 2009-002693 A | 1/2009 |
| JP | 2011-080814 A | 4/2011 |
| JP | 2015-086866 A | 5/2015 |
| JP | 2016-113819 A | 6/2016 |
| WO | 2011/065340 A1 | 6/2011 |

OTHER PUBLICATIONS

International Search Report of PCT/JP2017/040273 dated Feb. 6, 2018.

* cited by examiner

| ABNORMALITY CAUSE | VISCOSITY | DENSITY | DIELECTRIC CONSTANT |
|---|---|---|---|
| OIL DEGRADATION | — | ↑ | — |
| WATER CONTAMINATION | — | — | ↑↑ |
| SOOT CONTAMINATION | ↑ | — | ↑ |
| FUEL CONTAMINATION | ↓ | — | — |
| METAL POWDER CONTAMINATION | ↑ | ↑ | — |

MOVING AVERAGE

AMOUNT OF CHANGE PER UNIT TIME

DIFFERENCE IN AMOUNT OF CHANGE

OIL DIAGNOSIS SYSTEM

TECHNICAL FIELD

The present invention relates to an oil diagnosis system diagnosing abnormality of oil on the basis of oil properties of the oil detected by an oil sensor.

BACKGROUND ART

In recent years, attempts have been made to apply abnormality diagnosis to work machines including hydraulic excavators, dump trucks, wheel loaders, fork lifts, and cranes, on the basis of sensor value data from an oil sensor provided in the work machine.

For example, Patent Document 1 discloses a diagnosis system for oil properties in a work machine, the diagnosis system including a storage device storing a plurality of pieces of sensor data input from an oil sensor sensing the oil properties of oil utilized to operate the work machine and determination values specified for the respective pieces of sensor data, and a calculation processing device executing first processing of determining a degree of abnormality of the oil on the basis of the plurality of pieces of sensor data and the determination values related to the plurality of pieces of sensor data, second processing of determining a need for oil analysis involving oil extraction on the basis of the degree of abnormality of the oil determined in the first processing, and third processing including, in a case where the second processing determines the need for oil analysis involving the oil extraction, outputting the determination to another terminal.

PRIOR ART DOCUMENT

Patent Document

Patent Document 1: JP-2016-113819-A

SUMMARY OF THE INVENTION

Problem to be Solved by the Invention

Patent Document 1 described above discloses a method of converting the pieces of sensor data obtained from the oil sensor into evaluation values ($\Delta Yj(t)$) via a predetermined equation (evaluation formula), classifying the evaluation values into a plurality of ranks on the basis of the determination values, and identifying the cause of abnormality of the oil on the basis of the "rank of the evaluation value."

However, the identification, by an oil analysis company, of the cause of the abnormality based on the rank of the evaluation value has room for improvement in terms of accuracy, and is preferably implemented in conjunction with oil analysis in order to achieve sufficient accuracy. In a case where an abnormality is found, a technical service person performs repair and maintenance work in accordance with the cause of the abnormality. Thus, the technical service person performs appropriate maintenance work on the work machine after the cause is identified by oil analysis. This precludes appropriate maintenance work from being promptly performed at the stage of the first processing of determining the degree of abnormality in oil.

An object of the present invention is to provide an oil diagnosis system capable of identifying the cause of the abnormality of the oil without implementing oil analysis.

Means for Solving the Problem

The present application includes a plurality of means for solving the above-described problem, and an example of the means is an oil diagnosis system including a controller diagnosing a machine on a basis of pieces of sensor data about a plurality of oil properties acquired via an oil sensor mounted in the machine, the oil properties including a viscosity, a density, and a dielectric constant of oil, the controller including a storage section configure to store amount-of-change determination values specified for respective amount-of-change indexes indicative of tendencies of temporal changes in the pieces of sensor data about the plurality of oil properties, an abnormality determining section configured to determine abnormality of the oil on a basis of the pieces of sensor data about the plurality of oil properties and abnormality determination values prescribed for the respective pieces of sensor data about the plurality of oil properties, a cause identifying section configured to identify, when the oil is determined to be abnormal, a cause of the abnormality of the oil on a basis of a type of the oil property determined to be abnormal and the amount-of-change determination value of the oil property, and a transmission section configured to transmit, to other terminal, a result for the cause of the abnormality identified by the cause identifying section.

Advantages of the Invention

According to the present invention, the cause of the abnormality of the oil can be promptly determined without implementation of oil analysis.

MODES FOR CARRYING OUT THE INVENTION

Figure 1:
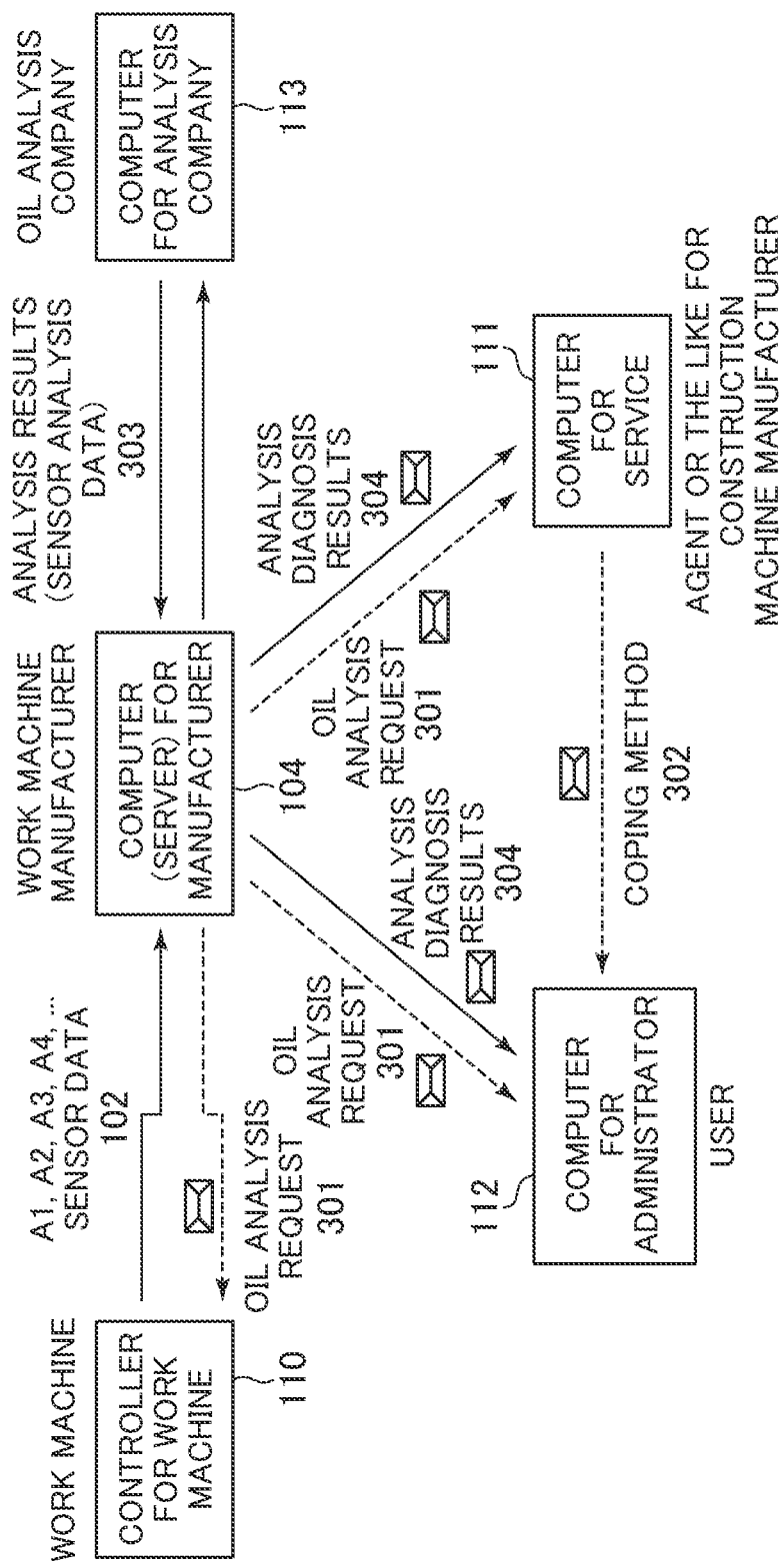
FIG. 1 is a schematic configuration diagram of an oil diagnosis system according to an embodiment of the present invention.

In an engine mounted in machines such as work machines including hydraulic excavators, and hydraulic equipment such as hydraulic pumps and hydraulic cylinders, for example, repetition of high-load operations such as excavation degrades the very properties of oil (engine oil or hydraulic oil) used for lubrication of components and as a power transmission medium. Additionally, degraded lubrication performance of the oil leads to defects such as wear in contact portions of components subjected to high loads. For improved durability of components of an engine system or a hydraulic equipment system, the oil needs to be periodically changed in order to properly maintain the lubrication performance of the oil. Additionally, for example, fine abrasion powder generated on contact surfaces inside components due to high-load operations are collected by a filter provided in a return circuit for the oil to maintain cleanliness of the oil. However, degraded oil properties accumulate wear in the filter itself, leading to a need for periodic replacement of the filter itself. Additionally, significant damage to the components such as significant wear of the components lead to a need for replacement of the components themselves.

An oil diagnosis system according to the present embodiment uses a sensor to sense the state of the properties of oil used for lubrication of key components of an engine system or a hydraulic equipment system in machines such as work machines or as a power transmission medium for the components, determines the degree of abnormality of the oil in real time on the basis of sensor data about the properties (numerical values indicative of a physiochemical state of the oil), presents a coping manual for repair and maintenance work to be performed in accordance with the result of the determination at an appropriate timing before the machine fails, and encourages oil extraction for detailed oil analysis as needed. Thus, oil change, replacement of a filter or components, or the like is properly performed to allow failures to be prevented, and coping processing such as repairs is promptly executed to allow the machine to be efficiently managed. Additionally, components can be recycled before a failure occurs, enabling minimization of the down-time and repair cost of the machine.

By way of example, embodiments utilizing a hydraulic excavator will be described below. However, the present invention is applicable not only to the hydraulic excavator but also to any machines utilizing oil as a lubricant or a power transmission medium, including other work machines such as dump trucks, wheel loaders, bulldozers, fork lifts, and cranes, as well as machines such as vehicles and industrial machines that utilize an engine. Additionally, by way of example, a system sensing the properties of engine oil will be described. However, the present invention is directed not only to engine oil but also to hydraulic oil for driving of a hydraulic actuator, or mission oil, or the like.

FIG. 1 is a schematic configuration diagram of an oil diagnosis system according to an embodiment of the present invention. The diagnosis system illustrated in the figure includes a controller (controller for a work machine) 110 mounted in a hydraulic excavator 501 (see FIG. 2) utilized by a user, a computer (server) 104 for a manufacturer managed by a manufacturer manufacturing the hydraulic excavator 501 and including a controller 104a and a storage device (database (storage section)) 104b, a computer (computer for a administrator) 112 used by the administrator (user) of the hydraulic excavator 501, a computer (computer for service) 111 used by a technical service person belonging to a work machine manufacturer or a sales office, an agent, or the like of the manufacturer, the technical service person performing repairs and maintenance work on the hydraulic excavator 501, and a computer 113 for an analysis company managed by an oil analysis company analyzing oil extracted from the hydraulic excavator 501.

Note that, although not illustrated in the drawings, the controller 110 and the computers 104, 112, 111, and 113 include a calculation processing device (for example, a CPU) serving as calculation means for executing various programs, a storage device (for example, semiconductor memory such as a ROM, a RAM, and a flash memory, a magnetic storage device such as a hard disk drive (storage section)) serving as storage means for storing various data including the programs, and an input/output calculation processing device for controlling input and output of data, instructions, and the like to and from the calculation processing device, the storage device, and the like. Additionally, the controller 110 and the computers 104, 112, 111, and 113 are connected by radio or wire to a network (for example, a LAN, a WAN, and the Internet) and configured to be able to transmit and receive data to and from one another. Furthermore, the controller 110 and the computers 104, 112, 111, and 113 may include a display device (for example, a liquid crystal monitor) configured to display the results of processing by the calculation processing device in a case where information needs to be provided to persons including operators of the controller 110 and the computers 104, 112, 111, and 113, and may include an input device (for example, ten keys, a keyboard, or a touch panel) in a case where the persons need to input data). Additionally, as the computers 104, 112, 111, and 113 constituting the present diagnosis system, portable terminals (notebook personal computers, cellular phones, smartphones, tablet terminals, and the like) can be utilized as well as stationary terminals.

Figure 2:
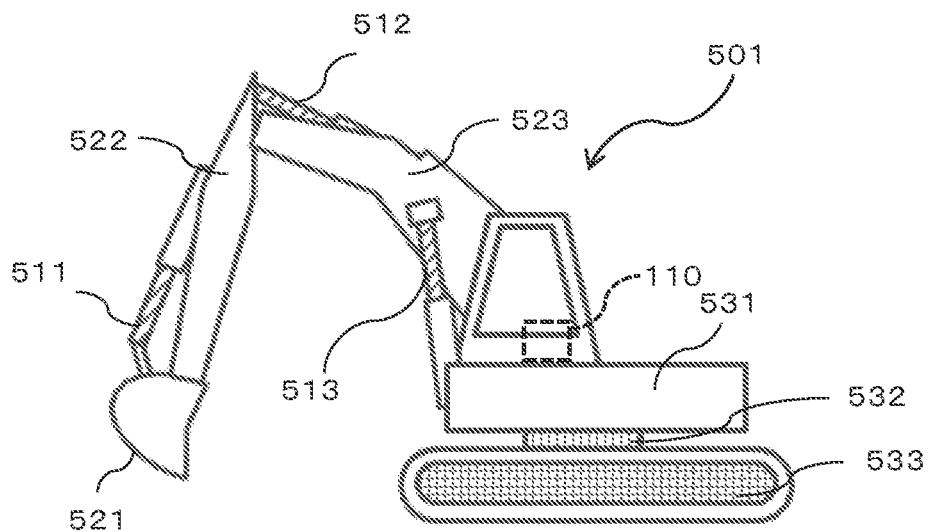
FIG. 2 is a general configuration diagram of a hydraulic excavator 501.

FIG. 2 illustrates a general configuration diagram of the hydraulic excavator 501. The hydraulic excavator 501 includes an oil property sensor 101A (illustrated in FIG. 3), a controller 110 for the work machine, hydraulic cylinders 511, 512, and 513 configured to drive a bucket 521, an arm 522, and a boom 523, a hydraulic pump 702 (see FIG. 3) configured to feed hydraulic oil to hydraulic actuators in the hydraulic excavator including the hydraulic cylinders 511, 512, and 513, an engine 701 (see FIG. 3) driving the hydraulic pump 702, a lower travel structure 533 including crawlers (endless tracks) driven by a traveling hydraulic motor (not illustrated), and an upper swing structure 531 swingably attached to an upper portion of the lower travel structure 533 via a swing mechanism 532 and swung and driven by a swing hydraulic motor (not illustrated).

Operations of the hydraulic excavator 501 will be described. In a case where the hydraulic excavator 501 performs an operation such as excavation, the hydraulic cylinders 511, 512, and 513 perform an extending and contracting operation to drive the bucket 521, the arm 522, and the boom 523. A base of the boom 523 is attached to the upper swing structure 531.

Figure 3:
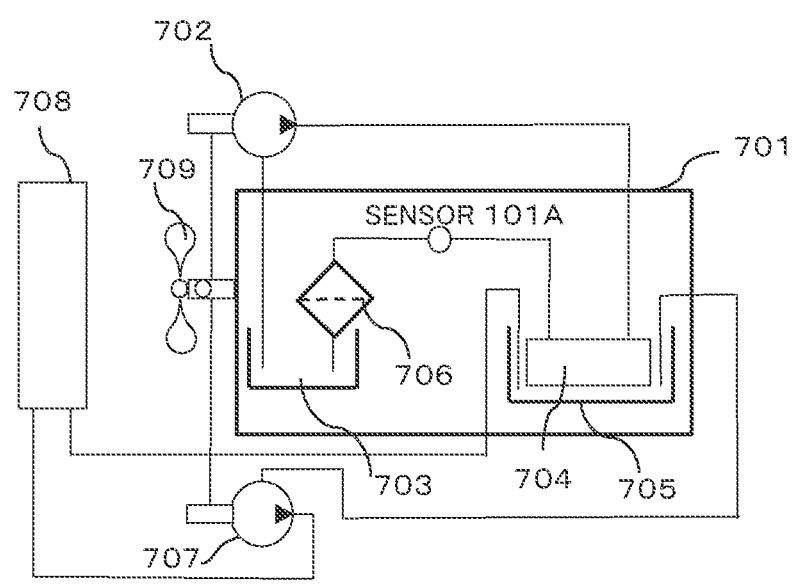
FIG. 3 is a configuration diagram of an oil system of an engine 701 in the hydraulic excavator 501.

FIG. 3 is a configuration diagram of a system for engine oil utilized in the engine 701 of the hydraulic excavator 501. The engine oil is used to lubricate the inside of the engine 701 and to cool the engine 701. In FIG. 3, an oil pump 702 is driven in accordance with rotation of the engine 701. The oil pump 702 sucks the engine oil from an oil pan 703 and feeds the engine oil to an oil cooler 704. The engine oil is cooled by the oil cooler 704 through heat exchange with cooling water in a water jacket 705, and after an oil filter 706 removes foreign matter from the cooled engine oil, the engine oil is returned to the oil pan 703.

Additionally, a water pump 707 is also driven by rotation of the engine 701 to suck the cooling water in the water jacket 705, and feeds the cooling water to a radiator 708. The cooling water cooled by the radiator is returned to the water jacket 705. The radiator 708 is cooled (air-cooled) by air taken in by a cooling fan 709 attached to a rotation section of the engine 701.

The oil property sensor (also referred to as the oil sensor) 101A is provided on an oil passage (return circuit) which connects the oil cooler 704 to the oil filter 706 and through which the engine oil passes when returning to the oil pan 703. The oil property sensor 101A senses (measures) the properties (specifically including the temperature, viscosity, density, and dielectric constant) of the engine oil passing through the oil passage. In the description of the present embodiment, the temperature, viscosity, density, and dielectric constant of the engine oil are sensed by the single oil property sensor 101A. However, the system may be configured such that sensing of the four properties is appropriately shared among a plurality of oil property sensors or the same property is sensed at different locations. In the former case, each oil property sensor senses one or more oil properties.

A sensor signal from the oil property sensor 101A is appropriately processed into data indicative of the physical amounts of the oil properties (oil property data or sensor data), which are input to and stored in the controller 110 for the work machine and the computer 104 for the manufacturer. In the present embodiment, the sensor data acquired by the oil property sensor 101A is temporarily stored in the storage device 103 of the controller 110 for the work machine and is output to the computer 104 for the manufacturer with a predetermined period and stored in the storage device (database (DB)) 104b that can be utilized by the computer 104 for the manufacturer. The sensor data may be stored not only in the storage device 104b but in any other storage device that can be utilized by the computer 104 for the manufacturer, including the storage device (for example, a hard disk drive or flash memory) in the computer 104 for the manufacturer. The storage device 104b may be a cloud database to which the computer 104 can be connected.

Note that the location where only the oil property sensor 101A is installed has been described for simplification of description but that the hydraulic excavator 501 may include oil property sensors other than the oil property sensor 101A, with the number of oil property sensors not particularly limited.

The oil properties measured by the oil property sensor 101A include the temperature, viscosity, density, and dielectric constant of the oil. Additionally, oil properties such as color data and a contamination grade for the oil may be added as objects to be measured, and additional oil property sensors may be installed as needed. The oil properties that can be measured by the oil property sensor vary according to the specifications of the sensor (some sensors can measure two or more oil properties instead of only one oil property), and thus, the combination of oil property sensors actually mounted in the hydraulic excavator 501 varies according to the oil properties to be measured and the specifications of each sensor.

Figure 4:
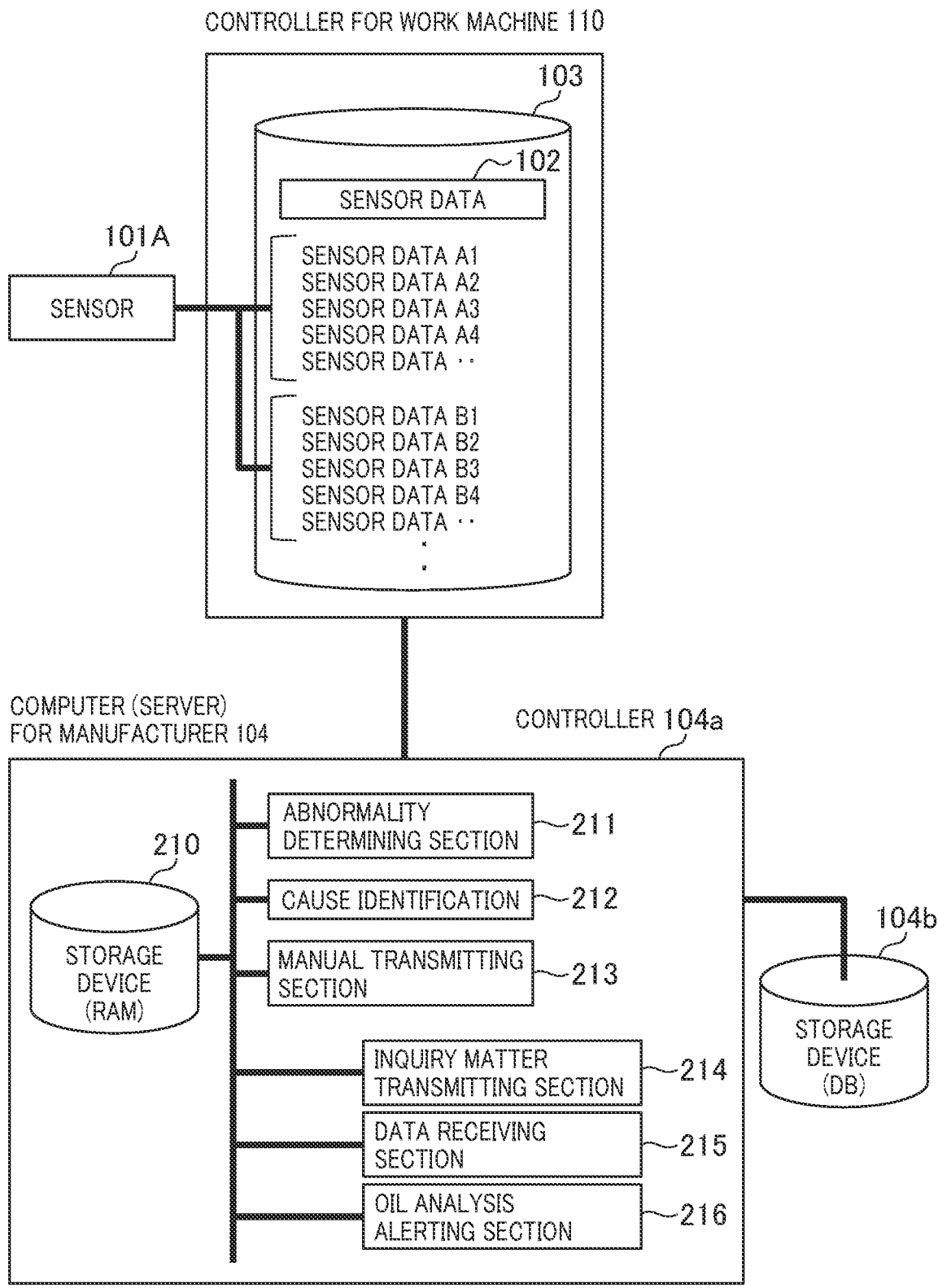
FIG. 4 is a schematic configuration diagram of a controller 110 for a work machine and a computer 104 for a manufacturer.

FIG. 4 is a schematic configuration diagram of the controller 110 for the work machine and the computer 104 for the manufacturer.

The controller 110 for the work machine includes a storage device 103 configured to store sensor data (first-level sensor data) 102 based on sensor values from the oil property sensor 101A mounted in the hydraulic excavator 501. The oil property sensor 101A according to the present embodiment can measure four oil properties including the temperature, the viscosity, the density, and the dielectric constant. As illustrated in FIG. 4, for example, sensor data acquired by the sensor 101A at a certain point in time is appropriately processed by the controller 110 for the work machine and is stored, as pieces of sensor data A1, in the storage device 103 of the controller 110 for the work machine in association with the point in time of measurement. The pieces of sensor data A1, A2, A3, A4, . . . indicate the pieces of sensor data about the viscosity measured by the sensor 101A at different points in time, and the trailing number of reference sign of the sensor data increases over time. Thus, time-series data about the sensor data A of the viscosity acquired by the sensor 101A is stored in the controller 110 for the work machine. Similarly, illustrated sensor data B is indicative of sensor data about the density acquired by the sensor 101A. Although description is omitted, the other properties sensed by the sensor 101A, the dielectric constant and the temperature, are similarly stored in the storage device 103 as pieces of sensor data C and D.

The controller 104a of the computer (server) 104 for the manufacturer includes: a storage device (RAM) 210 storing amount-of-change determination values that are determination values (thresholds) for determining whether temporal changes in the pieces of sensor data A, B, and C that are sensed data about the viscosity, density, and dielectric constant of the engine oil acquired by the oil property sensor 101A are significant in identifying the cause of abnormality of the oil, the amount-of-change determination values being specified for respective amount-of-change index values (described below) indicative of tendencies of temporal changes in the pieces of sensor data A, B, and C; an abnormality determining section 211 executing processing of determining whether the engine oil is abnormal or not on the basis of the pieces of sensor data A, B, and C and abnormality determination values (described below) prescribed for the respective three oil properties (pieces of sensor data A, B, and C); a cause identifying section 212 executing, when the abnormality determining section 211 determines the oil to be abnormal, processing of identifying the cause of the abnormality of the oil on the basis of the type of the oil determined to be abnormal, the amount-of-change index values indicative of the tendencies of temporal changes in the pieces of sensor data A, B, and C, and the amount-of-change determination values stored in the storage device 210; and a manual transmitting section 213 executing processing of transmitting, to another terminal (for example, at least one of the controller 110 for the work machine, the computer 112 for the administrator, and the computer 111 for service), a coping manual for repairs and maintenance work corresponding to the cause identified by the cause identifying section 202.

Furthermore, the computer 104 for the manufacturer includes: an inquiry matter transmitting section 214 executing processing of transmitting, to the another terminal (for example, at least one of the controller 110 for the work machine, the computer 112 for the administrator, and the computer 111 for service), inquiry matters related to the presence or absence of abnormality in the hydraulic excavator 501 when the cause identifying section 202 fails to identify the cause of the abnormality of the oil by using the type of the oil determined to be abnormal, the amount-of-change index values for the pieces of sensor data A, B, and C, and the amount-of-change determination values; and an data receiving section 215 receiving answers to the inquiry matters from a user of the another terminal having received the inquiry matters, the answers to the inquiry matters being transmitted from the another terminal; and an oil analysis alerting section 216 executing processing of transmitting, to the another terminal (for example, at least one of the controller 110 for the work machine, the computer 112 for the administrator, the computer 111 for service, and the computer 113 for the analysis company), a need for oil analysis involving oil extraction when the cause identifying section 212 fails to identify the cause of the abnormality of the oil by using the type of the oil determined to be abnormal, the amount-of-change index values for the pieces of sensor data A, B, and C, the amount-of-change determination values, and the answers to the inquiry matters.

The storage device 210 of the computer 104 for the manufacturer stores the abnormality determination values (threshold) utilized when the abnormality determining section 211 determines whether the oil is abnormal or not on the basis of the oil properties. The abnormality determination values are prescribed for the respective oil properties. In other words, the abnormality determination value is specified for each of the viscosity, the density, and the dielectric constant. The abnormality determination value for each oil property is not limited to a single value, and two abnormality determination values may be prescribed for each oil property. Each abnormality determination value is specified on the basis of a record of a correlation between the degree of abnormality of the oil and past sensor data (oil property data) acquired from the hydraulic excavator 501 and a hydraulic excavator of the same type.

In the present embodiment, as the abnormality determination value for the viscosity, two abnormality determination values are prescribed, an upper abnormality determination value SAh larger than a normal initial value and a lower abnormality determination value SAl smaller than the initial value. Additionally, for the density and the dielectric constant, only upper abnormality determination values SBh and SCh larger than initial values are prescribed. Accordingly, for the viscosity, the abnormality determining section 211 determines abnormality when the value of the sensor data A is larger than the upper abnormality determination value SAh and when the value of the sensor data A is smaller than the lower abnormality determination value SAl. Additionally, for the density and the dielectric constant, the abnormality determining section 211 determines abnormality when the values of the sensor data B and the sensor data C are respectively larger than the abnormality determination values SBh and SCh.

Note that a value may be set by multiplying each abnormality determination value by a predetermined rate and that the system may be configured such that, when the sensor data value is larger or smaller than the set value, a notification is provided indicating that abnormality is predicted to occur in the near future and that attention needs to be paid.

Figure 5:
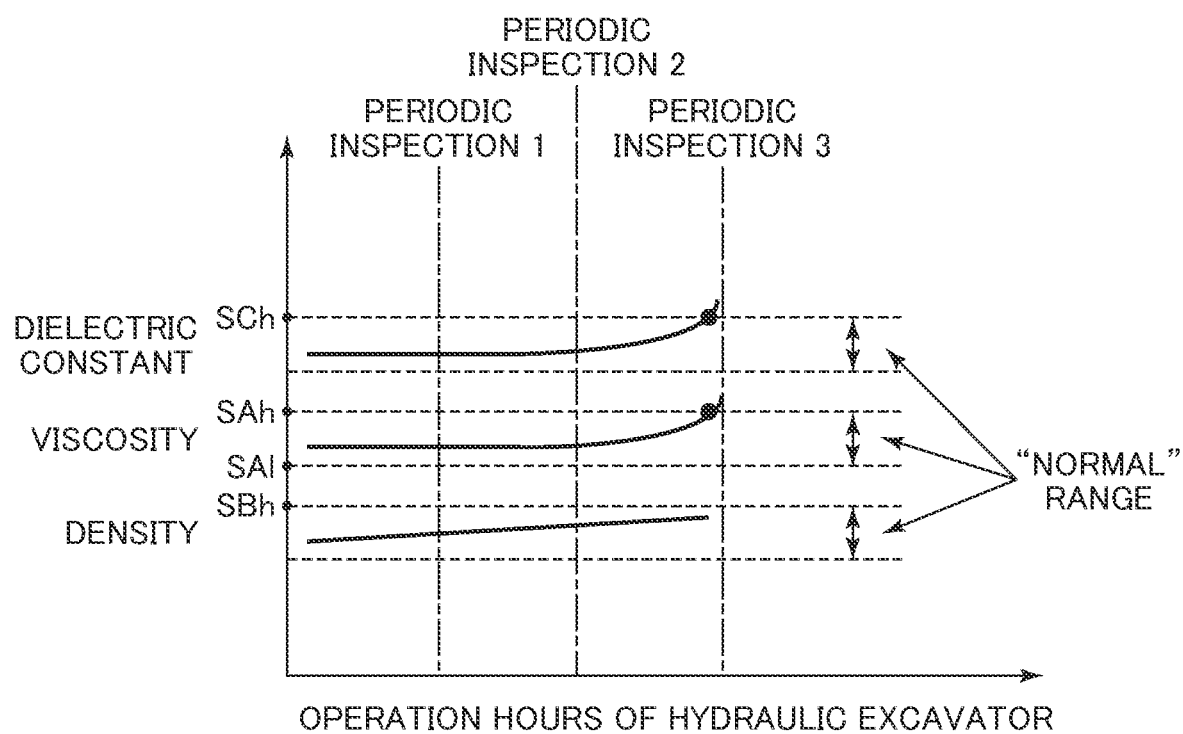
FIG. 5 is a diagram illustrating temporal changes in pieces of sensor data (viscosity, density, and dielectric constant) detected by a sensor 101A.

FIG. 5 is a diagram illustrating temporal changes in the viscosity (sensor data A), density (sensor data B), and dielectric constant (sensor data C) measured by the sensor 101A. FIG. 5 indicates the abnormality determination values SAh, SAl, SBh, and SCh for the viscosity (sensor data A), the density (sensor data B), and the dielectric constant (sensor data C).

The abnormality determining section 211 compares the pieces of sensor data A, B, and C (oil property data) acquired by the sensor 101A and the abnormality determination values SAh, SAl, SBh, and SCh to determine a magnitude relationship, thus determining whether the corresponding oil property is "normal" or "abnormal."

Figure 6:
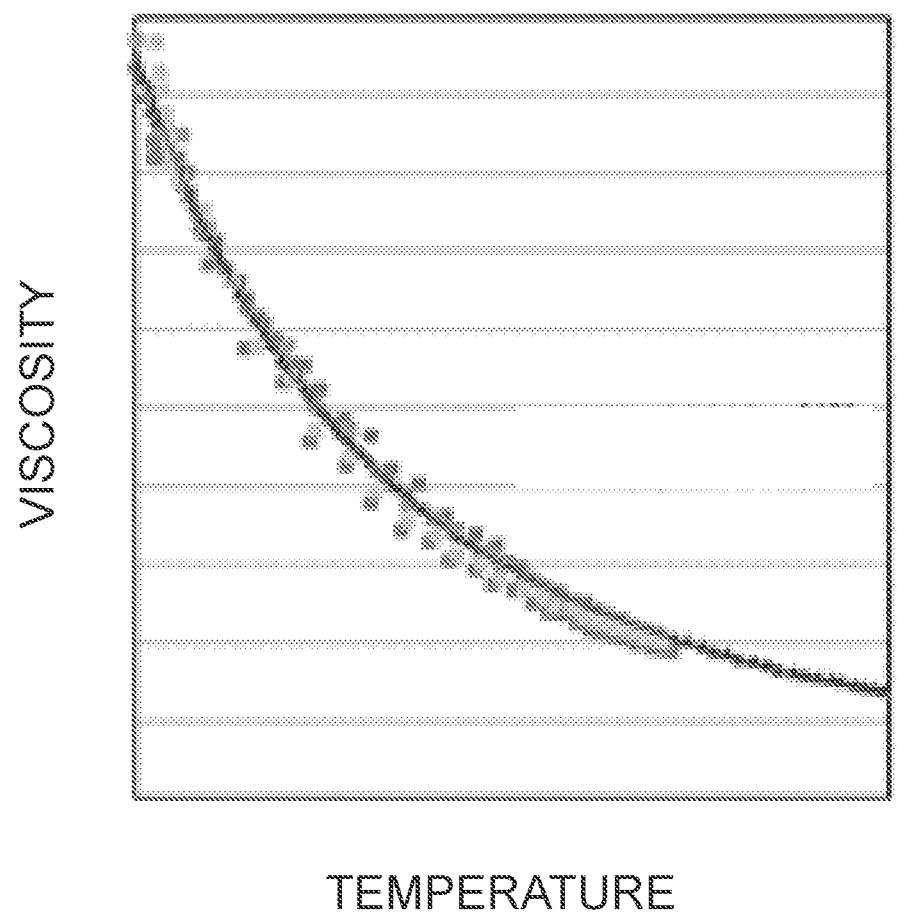
FIG. 6 is a diagram indicating a correlation between the viscosity (an example of the oil properties detected by the sensor 101A) and temperature.

FIG. 6 is a diagram indicating a correlation between the viscosity, which is one of the oil properties, and the temperature. The figure indicates that the viscosity is a characteristic value varying depending on the temperature. The other oil properties (density and dielectric constant) sensed by the sensor 101A also depend on the temperature, similarly to the viscosity in FIG. 6. Thus, the abnormality determining section 211 in the present embodiment converts a measured value $X_i(t)$ for each oil property acquired by the sensor 101A at an optional temperature t into the following third-order polynomial (Equation (1)) before comparing the abnormality determination values SAh, SAl, SBh, and SCh with the pieces of sensor data A, B, and C related to the oil properties. Thus, a measured value from the sensor 101A can be converted into a value in a predetermined temperature range at a practically significant accuracy, for example, a value in a temperature range assumed for the abnormality determination value. The abnormality determining section 211 determines whether the oil is abnormal or not by comparing the abnormality determination value with the value $X_i(t)$ resulting from the conversion based on (Equation 1). The cause identifying section 212 described below also determines the cause of the abnormality of the oil on the basis of the value $X_i(t)$ resulting from the conversion based on (Equation 1). Note that the subscript i in (Equation 1) is an integer of 1 or larger and is indicative of the type of the oil property. For example, the viscosity is designated as $X_1$, the density is designated as $X_2$, and the dielectric constant is designated as $X_3$. Additionally, box, $b_{1i}$, $b_{2i}$, and $b_{3i}$ are coefficients.

$$Xi(t) = b_{0i} + b_{1i} \cdot t + b_{2i} \cdot t^2 + b_{3i} \cdot t^3 \qquad \text{(Equation 1)}$$

Additionally, the sensor data about the oil properties relatively independent of the temperature (for example, the color data and contamination grade) can be expressed in the form of (Equation 1) similarly to the sensor data about the oil properties dependent on the temperature by adjusting the coefficients in the second and subsequent items in (Equation 1) described above.

Figures 7, 8:
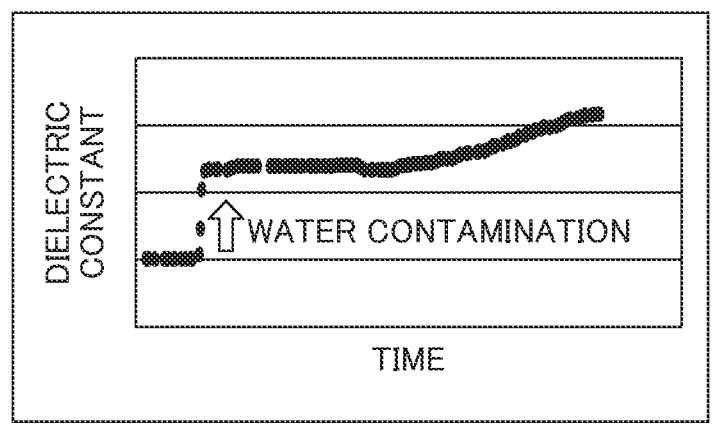
FIG. 7 is a diagram of a summary of correlations between the causes of abnormality of typical engine oil and variation in oil properties.
FIG. 8 is a diagram illustrating an example of temporal change in dielectric constant when the oil is contaminated with water.

Now, the cause identifying section 212 will be described. The cause identifying section 212 in the present embodiment identifies the cause of the abnormality utilizing the correlation between the cause of the abnormality and variation in oil property as indicated in FIG. 7. FIG. 7 is a map indicating correlations between the causes of abnormality of typical engine oil and variation in oil properties, based on experiment, performance data, and the like. In FIG. 7, the directions of arrows indicate directions in which the oil property (sensor data) changes. In other words, the up arrow indicates an increase in the numerical value of the sensor data acquired by the oil property sensor 101A, and the down arrow indicates a decrease in the numerical value of the sensor data. Additionally, the number of arrows is indicative of the magnitude of change in the numerical value of the sensor data during a predetermined time. Additionally, the sign "−" in the figure indicates that the oil property is in the normal range. Thus, FIG. 7 indicates that the value of the density increases with progression of degradation of the oil and that contamination of the oil with water rapidly increases the value of the dielectric constant and that contamination of the oil with soot increases the values of the viscosity and the dielectric constant and that contamination of the oil with fuel reduces the value of the density and that contamination of the oil with metal powder increases the values of the viscosity and the density.

FIG. 8 illustrates an example of temporal change in dielectric constant in a case where the oil is contaminated with water. Contamination of the oil with an amount of water sufficient to affect equipment mostly suddenly occurs due to damage to a packing, and in such a case, the dielectric constant rapidly increases during a short time as indicated in FIG. 8. Accordingly, for example, in a case where a rapid increase in time differential value of the dielectric constant or in the value of a difference in dielectric constant between different points in time is observed, the cause can be determined to be water contamination.

On the basis of such a fact, the present inventors have found the presence of abnormality the cause of which can be identified by focusing on temporal changes (increase and decrease) in the pieces of sensor data A, B, and C of the oil properties acquired by the oil property sensor and the combination of the temporal changes. Thus, the cause identifying section 212 of the computer 104 for the manufacturer uses index values referred to as the amount-of-change index values to determine the tendencies of temporal changes in the pieces of sensor data A, B, and C of the oil properties. Furthermore, the determination values (in the present specification, referred to as amount-of-change determination values) are set as the amount-of-change index value, the determination values being used to determine whether temporal changes in the pieces of sensor data A, B, and C indicated by the amount-of-change index values are significant in identifying the cause of the abnormality of the oil (that is, whether the temporal changes correspond to changes indicated by the arrows in FIG. 7). Then, the presence or absence of the changes (increase and decrease) in oil property illustrated in FIG. 7 is determined on the basis of the amount-of-change index values of the sensor data about the oil properties and the corresponding amount-of-change determination values, and the combination of the determined changes in oil properties is checked against the items in FIG. 7 to identify the cause of the abnormality.

Figure 9:
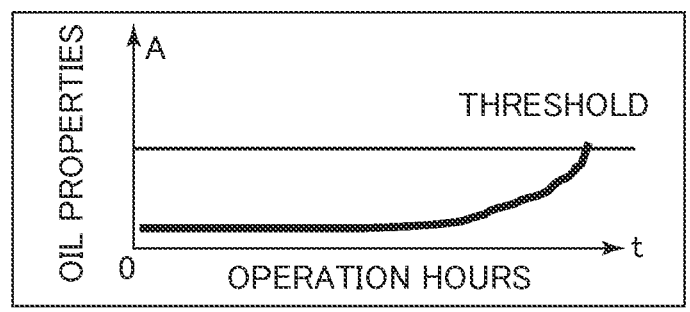
FIG. 9 is a descriptive diagram of an example of an amount-of-change index value.
Figure 9:
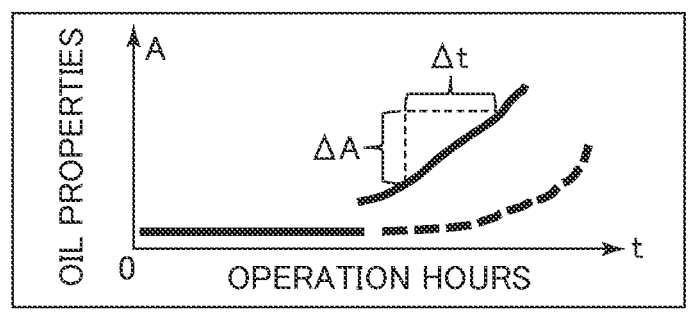
Figure 9:
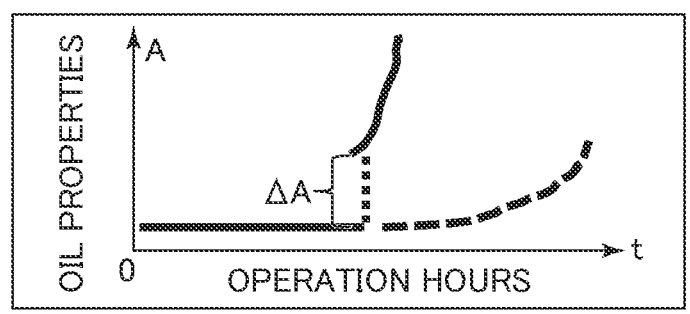

The cause identifying section 212 calculates the amount-of-change index values of the pieces of sensor data A, B, and C on the basis of the time series of the pieces of sensor data A, B, and C stored in the storage device 104b. FIG. 9 is a descriptive diagram of an example of amount-of-change index values of the sensor data utilized in the present embodiment. The amount-of-change index values that can be utilized in the present embodiment include (1) a "moving average" obtained by sequentially determining the time-series average value of a predetermined number of pieces of sensor data, (2) the "amount of change per unit time" obtained from the amount of change in sensor data per unit time (time differential value of the sensor data), and (3) the "difference of the amount of change" obtained from the difference between two pieces of sensor data obtained at different sensing points in time. For example, the use of the "moving average" reduces variation in sensor data to allow the trend of the sensor data over time to be easily determined. Additionally, the use of the "difference of the amount of change" allows a rapid change in sensor data in a short time to be easily determined. FIG. 9 illustrates the (1) moving average in the upper stage, the (2) amount of change per unit time in the middle stage, and the (3) difference of the amount of change in the lower stage. Note that the amount-of-change index value utilized to identify the cause of the abnormality of the actual oil can be varied according to the cause of the abnormality. The index values other than the three index values illustrated in FIG. 9 (for example, the time differential value of the amount of change per unit time) can also be utilized as long as the index values enable understanding of the tendencies of temporal changes in the pieces of sensor data A, B, and C.

For identification of the cause of the abnormality, which of the amount-of-change index values is utilized and what amount-of-change determination value is utilized can be set on the basis of time-series record values or experimental data for the sensor data about the oil properties associated with each cause of the abnormality. For example, selection of the amount-of-change index value will be described. The amount of increase in dielectric constant per unit time in a case of soot contamination in FIG. 7 has been found to be substantially constant and to increase more slowly than the amount of increase in dielectric constant per unit time in a case of water contamination as in FIG. 8. Thus, the "amount of change per unit time" is preferably used as an amount-of-change index value. Additionally, for water contamination, the "difference of the amount of change" is preferably utilized as an amount-of-change index value in order to grasp a rapid increase in dielectric constant. Note that it may be difficult to distinguish water contamination from soot contamination simply by using the dielectric constant and that the amount of change in viscosity per unit time can thus be added as an amount-of-change threshold so as to determine the cause to be soot contamination in a case where an increase in viscosity per unit time is observed and otherwise to determine the cause to be water contamination.

Additionally, for a reduction in the adverse effect of outliers included in the sensor data, identification of the cause of the abnormality of the oil may involve taking, in advance, the moving average of the sensor data about each oil property and then calculating the amount of change per unit time and the difference of the amount of change. Furthermore, the use of the amount-of-change index values is not limited to the cause identifying section 212, but the abnormality determining section 211 may utilize the moving average of each oil property when determining whether the oil property is abnormal, and compare the moving average with each abnormality determination value to determine abnormality.

The transmission section 213 transmits, to the another terminal (for example, at least one of the controller 110 and the computers 111 and 112), the cause of the abnormality identified by the cause identifying section 212. At this time, a coping manual for repairs and maintenance work for coping with the cause of the abnormality is also transmitted to the another terminal. The coping manual is pre-specified for each cause of the abnormality and stored in the storage device 210 of the computer 104 for the manufacturer similarly to the sensor data and the like. Examples of maintenance work based on the coping manual include oil change, replacement of the oil filter, and inspection and replacement of components. Typically, it is assumed that a technical service person visits a site where the work machine to be maintained is in operation to implement matters described in the coping manual, and thus, the coping manual is preferably transmitted to the computer 111 for service. However, in a case where even the user (administrator) of the work machine to be maintained can easily implement the maintenance work, the downtime of the work machine can be minimized. Thus, depending on the contents of the manual, the manual may preferably be transmitted to the computer 112 for the administrator or the controller 110 for the work machine.

Figure 10:
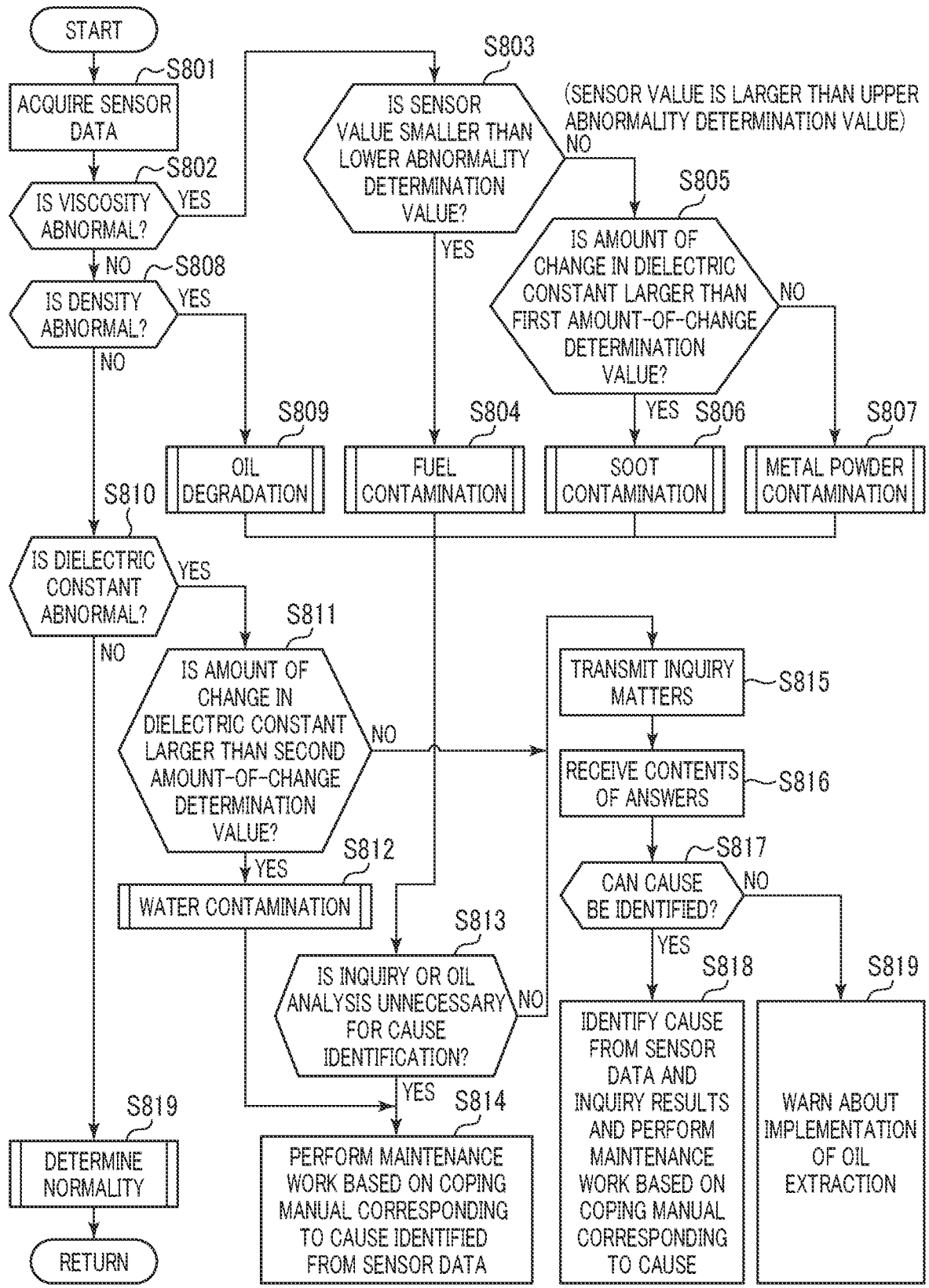
FIG. 10 is an example of a flowchart of processing executed by the computer 104 for the manufacturer.

Now, an example of a series of processing executed by the diagnosis system configured as described above will be described using FIG. 10. FIG. 10 is an example of a flowchart of processing executed by the computer 104 for the manufacturer in the present embodiment.

The computer 104 for the manufacturer invokes processing in the flowchart in FIG. 10 at predetermined time intervals (invocation cycles). For example, the computer 104 for the manufacturer invokes the processing when the engine is started and subsequently invokes the processing at predetermined time intervals (for example, at time intervals of one hour) until the engine is stopped.

In S801, the abnormality determining section 211 acquires the pieces of sensor data A, B, and C, and in S802, determines whether the viscosity is abnormal or not on the basis of the sensor data A of the viscosity and the abnormality determination values SAh and SAl. Specifically, in a case where the sensor data A of the viscosity is determined to be larger than the upper abnormality determination value SAh or smaller than the lower abnormality determination value SAl, the processing proceeds to S803, and otherwise the viscosity is determined to be normal and the processing proceeds to S808.

In S803, the cause identifying section 212 determines whether the value of the sensor data A is smaller than the lower abnormality determination value SAl. Here, in a case where the value of the sensor data A is determined to be smaller than the lower abnormality determination value SAl, the processing proceeds to S804. The cause identifying section 212 determines the cause of the abnormality of the oil (decrease in viscosity) to be "fuel contamination," and the processing proceeds to S813. On the other hand, in a case where the value of the sensor data A is determined to be larger than the upper abnormality determination value SAh, the processing proceeds to S805.

In S805, the cause identifying section 212 determines whether the amount-of-change index value for the dielectric constant (sensor data C) is larger than a first amount-of-change determination value or not to determine whether the amount of temporal change in dielectric constant (sensor data C) has increased or not. Here, the "amount of change per unit time" is utilized as the amount-of-change index value for the dielectric constant. The first amount-of-change determination value is a determination value for determining whether the amount of change in dielectric constant (sensor data C) per unit time is indicative of an "increase in FIG. 7" or not. In other words, the cause identifying section 212 determines whether the amount of change per unit time is larger than the first amount-of-change determination value or not. In a case where the amount of change in dielectric constant per unit time can be confirmed to be larger than the first amount-of-change determination value, leading to the determination that the amount of temporal change in dielectric constant has increased, the processing proceeds to S806. The cause identifying section 212 determines the cause of the abnormality of the oil (increase in viscosity and increase in dielectric constant) to be "soot contamination," and the processing proceeds to S813. On the other hand, in a case where the amount of change in dielectric constant per unit time is not larger than the first amount-of-change determination value, the processing proceeds to S807, and the cause identifying section 212 determines the cause of the abnormality of the oil (increase in viscosity) to be "metal powder contamination," and the processing proceeds to S813.

In S813, when identifying, as the actual cause of the abnormality, the cause of the abnormality temporarily determined in S804, S806, S807, and S809, the cause identifying section 212 determines whether an inquiry to persons related to the hydraulic excavator 501 or oil analysis is needed. In the present embodiment, the determination involves focusing on the amount of temporal change in oil property referenced to reach the determination in S804, S806, S807, and S809 and confirming whether the amount of change in the oil property per unit time (amount-of-change index value) is larger than that in the ordinary case of abnormality. In a case where the amount-of-change index value is larger than in the ordinary case of abnormality, the cause of the abnormality can be determined to be the actual cause of the abnormality without implementation of an inquiry or oil analysis (that is, the inquiry and oil analysis are determined to be "unnecessary" and the cause of the abnormality in S804, S806, S807, and S809 is determined to be the actual cause of the abnormality), and the processing proceeds to S814. For example, in a case where fuel contamination is determined in S804, the amount of decrease in viscosity per unit time is calculated. In a case where the value of the amount of decrease is larger than a corresponding value obtained in the ordinary case of fuel contamination (that is, this value corresponds to the amount-of-change determination value), the cause of the abnormality is determined to be fuel contamination, and the processing proceeds to S814. Additionally, in a case where soot contamination is determined in S806, the amount of increase in dielectric constant per unit time is calculated. In a case where the value of the amount of increase is larger than a corresponding value obtained in the ordinary case of soot contamination (amount-of-change determination value), the cause of the abnormality is determined to be soot contamination, and the processing proceeds to S814. Additionally, in a case where metal powder contamination is determined in S807, the amount of increase in viscosity per unit time is calculated. In a case where the value of the amount of increase is larger than a corresponding value obtained in the ordinary case of metal powder contamination (amount-of-change determination value), the cause of the abnormality is determined to be metal powder contamination, and the processing proceeds to S814. Additionally, in a case where oil degradation is determined in S809, the amount of increase in density per unit time is calculated. In a case where the value of the amount of increase is larger than a corresponding value obtained in the ordinary case of oil degradation (amount-of-change determination value), the cause of the abnormality is determined to be oil degradation, and the processing proceeds to S814.

On the other hand, in a case where the amount of change in oil property per unit time (amount-of-change index value) referenced to reach the determination in S804, S806, S807, and S809 is equal to or smaller than a corresponding value obtained in the ordinary case of abnormality, the inquiry to persons related to the hydraulic excavator 501 or the oil analysis is determined to be necessary. The processing proceeds to S815.

In S808, the abnormality determining section 211 determines whether the density is abnormal or not on the basis of the sensor data B of the density and the abnormality determination value SBh. Specifically, in a case where the sensor data B of the density is determined to be larger than the abnormality determination value SBh, the processing proceeds to S809. Otherwise the density is determined to be normal, and the processing proceeds to S810.

In S809, the cause identifying section 212 determines that the cause of the abnormality of the oil (increase in density) is determined to be "oil degradation," and the processing proceeds to S813.

In S810, the abnormality determining section 211 determines whether the dielectric constant is abnormal or not on the basis of the sensor data C of the dielectric constant and the abnormality determination value SCh. Specifically, in a case where the sensor data C of the dielectric constant is determined to be larger than the abnormality determination value SCh, the processing proceeds to S811. Otherwise the three oil properties, the viscosity, the density, and the dielectric constant are all determined to be normal (S819). Subsequently, the processing returns to the start, and the system stands by until the next invocation cycle.

In S811, the cause identifying section 212 determines whether the amount-of-change index value for the dielectric constant (sensor data C) is larger than a second amount-of-change determination value or not to determine whether the amount of temporal change in dielectric constant (sensor data C) has rapidly increased. Here, the "difference of the amount of change" is utilized as the amount-of-change index value for the dielectric constant. The second amount-of-change determination value is a determination value for determining whether the difference of the amount of change in dielectric constant (sensor data C) is indicative of a "rapid increase in FIG. 7." In other words, the cause identifying section 212 determines whether the difference between two pieces of sensor data obtained at different sensing points in time is larger than the second amount-of-change determination value. In a case where the difference between two pieces of sensor data obtained at different sensing points in time can be confirmed to be larger than the second amount-of-change determination value, leading to the determination that the amount of temporal change in dielectric constant has rapidly increased, the proceeding proceeds to S812. The cause identifying section 212 identifies the cause of the abnormality of the oil (rapid increase in dielectric constant) as "water contamination," and the processing proceeds to S814. On the other hand, in a case where the difference of the amount of change in dielectric constant is not larger than the second amount-of-change determination value, the cause identifying section 212 determines, for the cause of the abnormality of the oil (increase in dielectric constant), the "impossibility of achieving the identification using only the sensor data," and the processing proceeds to S815.

In S814, the manual transmitting section 213 selects one of the coping manuals in the storage device 210 that is linked with the cause of the abnormality identified by the preceding processing (S804, S806, S807, and S809), and transmits the selected coping manual to another terminal (for example, at least one of the controller 110 and the computers 111 and 112). Accordingly, the user or the technical service person can implement repairs or maintenance work in accordance with the coping manual promptly after the abnormality is found, allowing prompt maintenance to be achieved without waiting for cause identification based on oil analysis as in the related art.

In S815, the inquiry matter transmitting section 214 transmits prepared inquiry matters to the computer 111 for service. The transmitted inquiry matters are related to the presence or absence of abnormality in the hydraulic excavator 501 and determined on the basis of the type of the oil property determined to be abnormal before S815 is reached, the amount-of-change index value calculated before S815 is reached, the result of a comparison between the amount-of-change index value and a corresponding amount-of-change threshold, the cause of the abnormality determined in S804, S806, S807, and S809, and the like.

Figure 11:
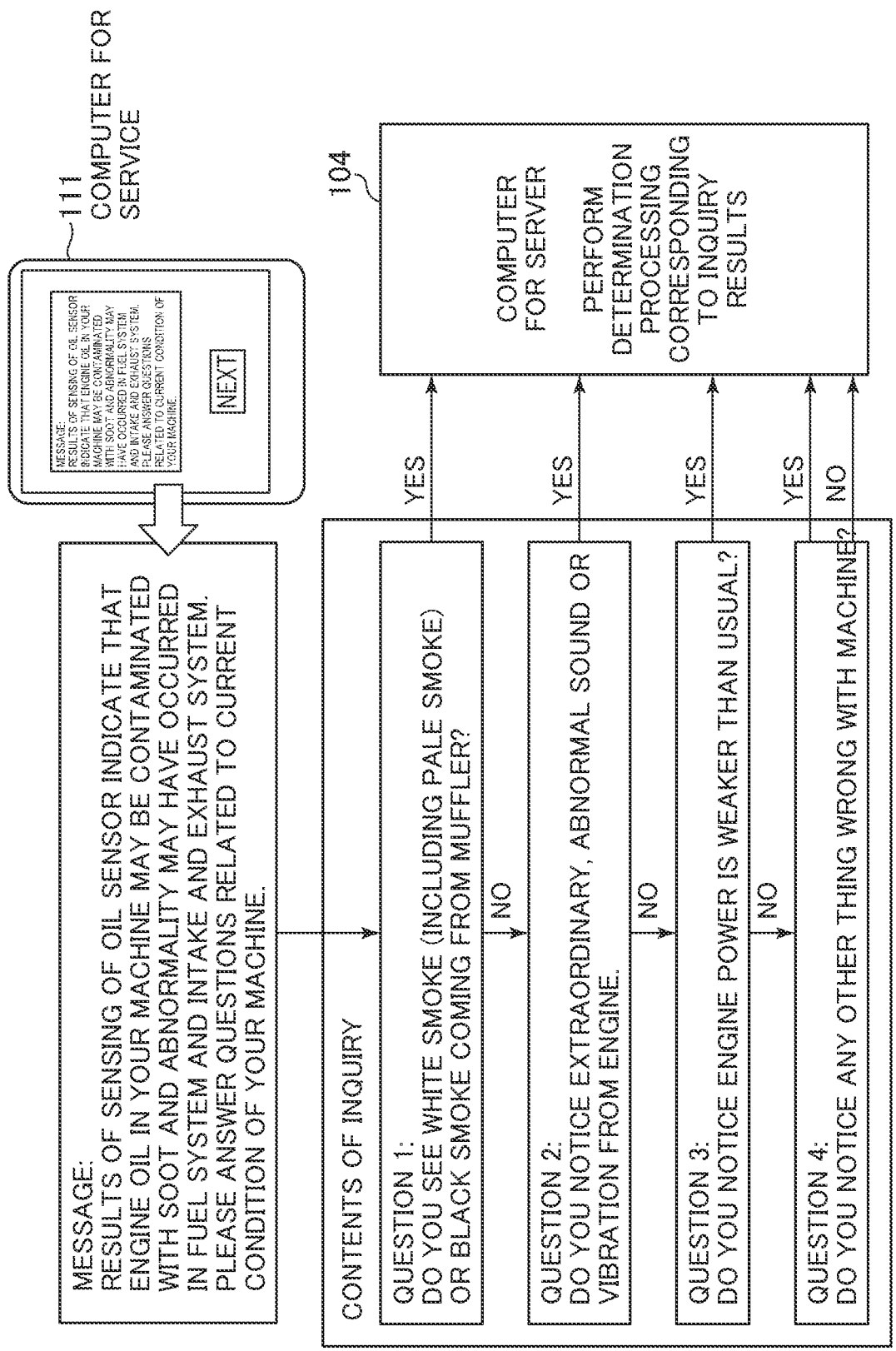
FIG. 11 is a descriptive diagram of an example of processing executed in S815 in a case where the likelihood of soot contamination is determined in S806.

FIG. 11 is a descriptive diagram of an example of processing executed in S815 in a case where the likelihood of soot contamination is determined in S806, and in this example, an inquiry is made as to whether a phenomenon is due to abnormality of equipment. First, in S815, when the computer 104 for the manufacturer (inquiry matter transmitting section 214) transmits the inquiry matters, a message is displayed on the computer 111 for service (tablet terminal) as illustrated in the upper stage of FIG. 11, the message reporting, to the administrator or user of the hydraulic excavator 501, an abnormality that can be determined from the current pieces of sensor data A, B, and C and requesting the technical service person to make an inquiry to the administrator or user. When the technical service person confirms the message, the contents of the inquiry to the administrator or the user are sequentially displayed on the computer 111 for service. In the example in FIG. 11, four questions are prepared. Specifically, question 1 is "Do you see white smoke (including pale smoke) or black smoke coming from the muffler?" Question 2 is "Do you notice extraordinary, abnormal sound or vibration from the engine?" Question 3 is "Do you notice engine power is weaker than usual?" Question 4 is "Do you notice any other thing wrong with the machine?" Answers to the inquiry are in YES/NO selection form. Each time the contents of the answers are input from the technical service person on the basis of the answers from the administrator or the user, the contents of the answers are transmitted from the computer 111 for service, and the computer 104 for the manufacturer receives the contents of the answers via the data receiving section 215 (S816).

In S817, the cause identifying section 212 determines whether or not the cause of the abnormality can be identified on the basis of the data acquired before S815 is reached and the contents of the answers received in S816. In the example in FIG. 11, in a case where any one of the four questions is responded with YES, the cause identifying section 212 determines that the cause of the abnormality can have been identified, and the processing proceeds to S818. In a case where all of the questions are responded with NO, the cause identifying section 212 determines that the cause of the abnormality cannot have been identified, and the processing proceeds to S819.

In S818, the cause identifying section 212 determines the cause of the abnormality on the basis of the data acquired before S815 is reached and the contents of the answers (results of the inquiry) received in S816. The manual transmitting section 213 selects one of the coping manuals in the storage device 210 that corresponds to the identified cause of the abnormality and transmits the selected coping manual to the computer 111 for service. Note that, in this case, when the coping manual is transmitted, an alert for oil extraction also may be output to the controller 110 and the computers 111, 112, and 113.

Figure 12:
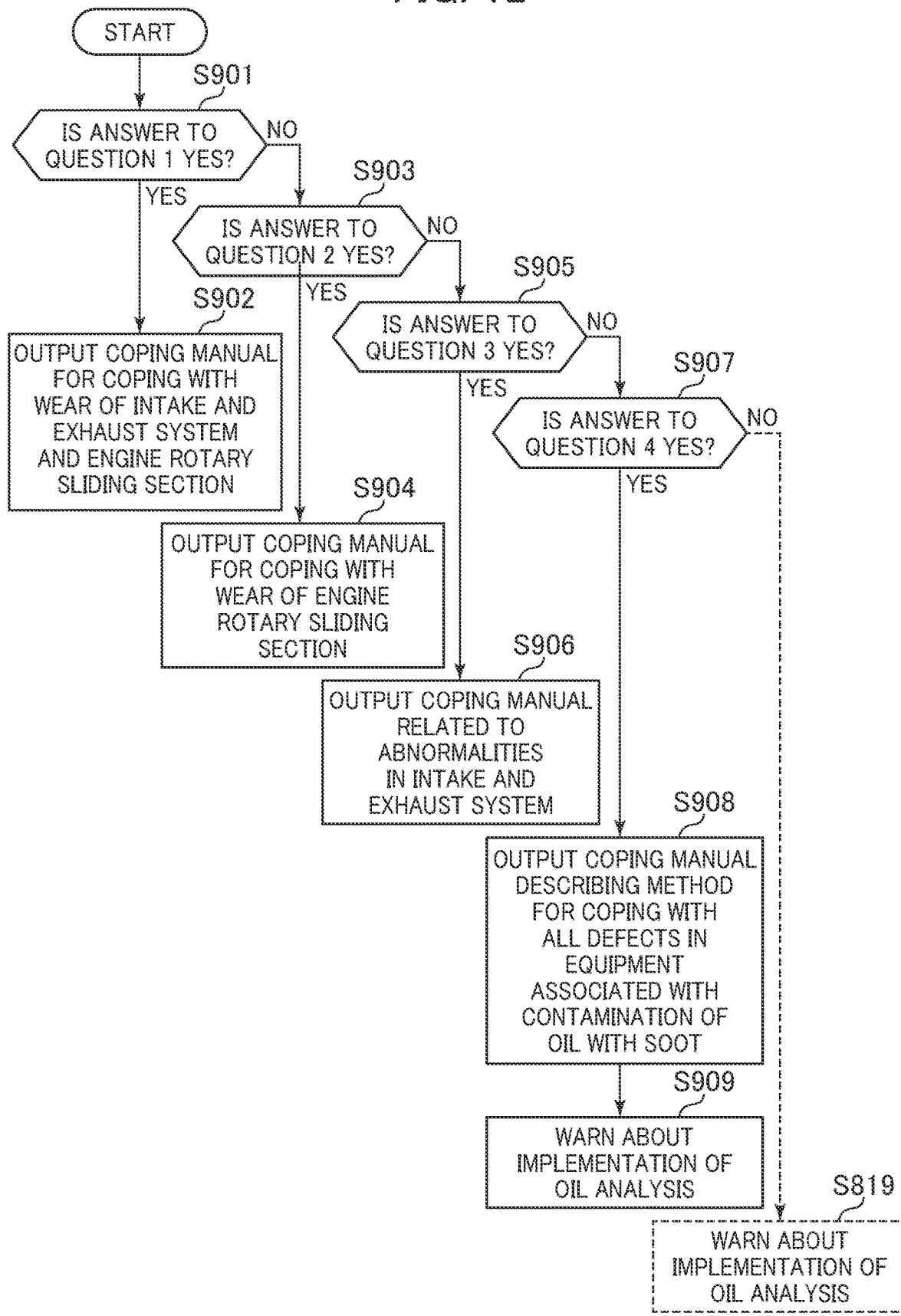
FIG. 12 is an example of a flowchart for a case where processing is selected in S818, the processing being executed by the computer 104 for the manufacturer in accordance with contents of answers to four inquiry matters in FIG. 11.

FIG. 12 is an example of a flowchart of a case where processing to be executed by the computer 104 for the manufacturer is selected according to the contents of the answers to the four inquiry matters in FIG. 11. Note that, in this case, it is assumed that the destination to which the coping manuals are output is the computer 111 for service.

In the flowchart in FIG. 12, the cause identifying section 212 first determines in S901 whether the answer to Question 1 is YES or not. In a case where the answer to Question 1 is YES, the manual transmitting section 213 outputs a manual for coping with wear of an intake and exhaust system and an engine rotary sliding section (S902), and the technical service person appropriately copes with the wear on the basis of the manual. On the other hand, in a case where the answer to Question 1 is NO, the processing proceeds to S903.

In S903, the cause identifying section 212 determines whether the answer to Question 2 is YES or not. In a case where the answer to Question 2 is YES, the manual transmitting section 213 outputs a manual for coping with wear of the engine rotary sliding section (S904), and the technical service person appropriately copes with the wear on the basis of the manual. On the other hand, in a case where the answer to Question 2 is NO, the processing proceeds to S905.

In S905, the he cause identifying section 212 determines whether the answer to Question 3 is YES or not. In a case where the answer to Question 3 is YES, the manual transmitting section 213 outputs a coping manual related to abnormalities in the intake and exhaust system (S906), and the technical service person appropriately copes with the abnormality on the basis of the manual. On the other hand, in a case where the answer to Question 3 is NO, the processing proceeds to S907.

In S907, the cause identifying section 212 determines whether the answer to Question 4 is YES or not (however, in a case where the above description is followed by the answer to Question 4 being NO (that is, in a case where the answers to all the questions are NO), the processing proceeds from S817 to S819). In a case where the answer to Question 4 is YES, the manual transmitting section 213 outputs a manual describing a method for coping with all defects in equipment associated with soot contamination (S908), and an alert for implementation of oil analysis is output to the computer 111 for service as in S819. Accordingly, the technical service person appropriately copes with the defect on the basis of the manual, and oil extraction for oil analysis is performed.

Note that, in the example in FIG. 11, the system is configured such that, in a case where YES is answered to a certain question, the subsequent questions are not displayed on the computer 111 for service. However, after all prepared questions are answered, what content of processing (for example, selection of the coping manual) is to be implemented in S818 may be determined.

Additionally, in S815 and S818 described above, the inquiry matters and the coping manual are transmitted to the computer 111 for service. However, the inquiry matters and the coping manual may be transmitted directly to the terminal of the user of the hydraulic excavator 501 (that is, the computer 112 for the administrator or the controller 110 for the work machine). In this case, the intervention of the technical service person is avoided, enabling an increase in efficiency and speed of the maintenance service.

In S819, the oil analysis alerting section 216 outputs an oil analysis request 301 to at least one of the controller 110 for the work machine, the computer 112 for the administrator, and the computer 111 for service, the oil analysis request 301 alerting oil analysis to request an oil analysis company to extract oil as promptly as possible and perform detailed oil analysis. The oil analysis alerting section 216 notifies the persons related to the hydraulic excavator 501 of the oil analysis request 301. Note that the oil analysis request 301 may also be transmitted to the computer 113 for the oil analysis company.

A specific example of the oil analysis request 301 is an e-mail. The e-mail contains a message encouraging implementation of oil extraction associated with oil analysis (for example, the message "please immediately extract and inspect oil"). Furthermore, in addition to the message, the e-mail may contain identification data about the hydraulic excavator from which the oil is to be extracted (for example, model name or a serial number), the operation hours of the hydraulic excavator (hour meter), and the point in time of output of the "abnormality determination" (point in time of the determination). The contents of descriptions in the e-mail need not be common to the computer 112 for the administrator and the computer 111 for service and may vary according to the position/role of a destination. Additionally, instead of the e-mail, a dedicated application may be automatically invoked to display similar contents on the application, or a dedicated alarm system may be operated by, for example, turning on, in a cab in the hydraulic excavator 501, a warning light encouraging oil analysis.

The oil analysis company performs detailed oil analysis on the basis of extracted oil, and transmits analysis results 303 (see FIG. 1) from the computer 113 for the analysis company to the computer 104 for the manufacturer (work machine manufacturer). The analysis results 303 include data (oil analysis data (also referred to as "second-level sensor data") obtained by analyzing the extracted oil in detail for the oil properties acquired by the sensor 101A, and the oil analysis data is sequentially accumulated in the storage device 210 of the computer 104 for the manufacturer. Note that the oil analysis company may transmit, along with the analysis results 303, diagnosis results 304 based on the analysis results 303 to the computer 104 for the manufacturer.

The work machine manufacturer receives the analysis results 303 and may then perform appropriate diagnosis on the basis of the analysis results. In that case, the analysis diagnosis results 304 and a manual (coping manual) for coping with the results are transmitted to the computer 111 for service, and the analysis diagnosis results 304 are also transmitted to the computer 112 for the administrator. The technical service person receives the coping manual, then visits the location of the hydraulic excavator 501, and performs maintenance work on the hydraulic excavator 501 on the basis of the coping manual. The maintenance work including oil change, replacement of the oil filter, and inspection and replacement of components. Note that, in a case where the maintenance work can be achieved by the user, the technical service person may transmit, instead of visiting the user for the maintenance work, a coping method to the user via an e-mail 302 (see FIG. 1) or the like to leave the maintenance work to the user. Note that, in the above description, communication between the two parties is performed via e-mail but that any communication means such as fax, telephone, or video call that is excellent in immediacy can be used instead. This also applies to any other communication between the controller and the computer included in the present embodiment and between the computers also included in the present embodiment. Additionally, the description assumes that oil extraction is performed by the user or the technical service person. However, oil extraction may be performed by the oil analysis company.

<Effects>

(1) In the above-described embodiment, the controller 104a of the computer 104 for the manufacturer includes: the storage device 210 storing determination values for determining whether temporal changes in the pieces of sensor data A, B, and C about the plurality of oil properties (viscosity, density, and dielectric constant) of the oil utilized in the hydraulic excavator 501 are significant in identifying the cause of the abnormality of the oil or not, the amount-of-change determination values being specified for the respective amount-of-change index values indicative of the tendencies of the temporal changes in the pieces of sensor data A, B, and C; the abnormality determining section 211 determining the abnormality of the oil on the basis of the pieces of sensor data A, B, and C about the plurality of oil properties and the abnormality determination values SAh, SAl, SBh, and SCh prescribed for the respective pieces of sensor data A, B, and C about the plurality of oil properties; the cause identifying section 212 identifying, when the abnormality determining section 211 determines the oil to be abnormal, the cause of the abnormality of the oil on the basis of the type of the oil property determined to be abnormal, the amount-of-change index values of the pieces of sensor data A, B, and C about the plurality of oil properties, and the amount-of-change determination values stored in the storage device 210; and the manual transmitting section 213 transmitting, to another terminal (for example, at least one of the controller 110 and the computers 111 and 112), the coping manual for coping with the cause identified by the cause identifying section 212.

In this configuration, the cause identifying section 212 of the computer 104 for the manufacturer determines the cause of the abnormality of the oil on the basis of the type of the oil property determined to be abnormal through sensing, the amount-of-change index values indicating the tendencies of temporal changes in the pieces of sensor data A, B, and C about the plurality of oil properties, and the amount-of-change determination values specified for the respective amount-of-change index values. Thus, the coping manual can be transmitted to another terminal including the computer 111 for service without implementation of oil extraction or oil analysis performed to identify the cause of the abnormality of the oil in the related art. Thus, for example, in a case where the cause of the abnormality is identified as contamination of the oil with metal powder, a coping manual describing a coping measure is promptly transmitted to the another terminal, and the user of the another terminal (for example, the technical service person) can implement the coping measures (for example, replacement of components) in accordance with the coping manual. Accordingly, according to the present embodiment, the efficiency and speed of the maintenance service can be increased. Additionally, in some cases (for example, in a case where easy component replacement is needed that can be sufficiently achieved by the user), the technical service person can transmit, instead of visiting the location of the hydraulic excavator 501, the coping manual from the computer 111 for service or the computer 104 for the manufacturer to the computer 112 for the administrator to have the user implement component replacement. This allows the abnormality to be eliminated without a need to wait for the technical service person to arrive. Thus, the present embodiment enables a reduction in service costs and component replacement costs, which corresponds to total life cycle costs, enabling a reduction in the down-time of the work machine and improvement of an operating rate.

(2) Furthermore, in the above-described embodiment, the controller 104a of the computer 104 for the manufacturer includes: the inquiry matter transmitting section 214 transmitting, to another terminal (for example, at least one of the controller 110 and the computers 111 and 112), inquiry matters related to the presence or absence of abnormality in the hydraulic excavator 501 when the cause identifying section 212 fails to identify the cause of the abnormality of the oil on the basis of the type of the oil property determined to be abnormal, and the amount-of-change determination values and the amount-of-change index values of the oil property; and the data receiving section 215 receiving answers to the inquiry matters transmitted from the another terminal. The cause identifying section 212 of the computer 104 for the manufacturer then identifies the cause of the abnormality of the oil on the basis of the answers to the inquiry matters, the type of the oil property determined to be abnormal, and the amount-of-change determination values and the amount-of-change index values of the oil property.

In this configuration, the cause of the abnormality of the oil is identified on the basis of the matters taken into account in the case of (1) described above as well as the answers to the inquiry matters. This configuration allows the abnormality to be identified in more opportunities than in the case of (1) described above. In this configuration, time is needed for transmission of the inquiry matters, answers to the inquiry matters, and reception of the answers. However, the coping manual can be transmitted earlier to another terminal than in a known procedure including implementation of oil extraction and analysis. This still enables a reduction in service costs and component replacement costs, and a reduction in the down-time of the work machine.

(3) Furthermore, in the above-described embodiment, for a case where the cause of the abnormality fails to be identified even by using the method described above in (2), the controller 104a of the computer 104 for the manufacturer includes the oil analysis alerting section 216 transmitting, to another terminal, the need for oil analysis involving oil extraction when the cause identifying section 212 fails to identify the cause of the abnormality of the oil on the basis of the answers to the inquiry matters and the amount-of-change determination values and the amount-of-change index values.

Thus, in the present embodiment, only when the cause of the abnormality fails to be identified even by using the methods in (1) and (2), oil extraction is warned to have the cause analyzed in detail on the basis of oil analysis. Thus, even when the cause of the abnormality fails to be identified by using the methods in (1) and (2), the cause of the abnormality can be identified on the basis of oil extraction and analysis.

(4) Additionally, the above-described embodiment provides the oil diagnosis system including the computer 104 for the manufacturer diagnosing the machine (hydraulic excavator) 501 on the basis of the pieces of sensor data A, B, and C about the plurality of oil properties acquired via the oil sensor 101A mounted in the machine 501, the oil properties including the viscosity, density, and dielectric constant of the oil, the oil diagnosis system including: the storage section (storage device) 210 storing the amount-of-change determination values specified for the respective amount-of-change index values indicative of the tendencies of temporal changes in the pieces of sensor data A, B, and C about the plurality of oil properties; the abnormality determining section 211 determining the abnormality of the oil on the basis of the pieces of sensor data A, B, and C about the plurality of oil properties and the abnormality determination values SAh, SAl, SBh, and SCh prescribed for the respective pieces of sensor data A, B, and C about the plurality of oil properties; the cause identifying section 212 identifying, when the abnormality determining section 211 determines the oil to be abnormal, the cause of the abnormality of the oil on the basis of the type of the oil property determined to be abnormal and the amount-of-change determination value of the oil property; and the transmission section 213 transmitting, to another terminal, the cause of the abnormality identified by the cause identifying section 212.

According to this configuration, the cause identifying section 212 of the computer 104 for the manufacturer can identify the cause of the abnormality of the oil on the basis of the type of the oil property determined to be abnormal through sensing, the amount-of-change index values indicating the tendencies of temporal changes in the pieces of sensor data A, B, and C about the plurality of oil properties, and the amount-of-change determination values specified for the respective amount-of-change index values.

Note that, by way of example, the connection form has been described in which, to achieve real-time abnormality monitoring, the controller 110 for the work machine and the computer 104 for the manufacturer can constantly communicate with each other. However, the system may be operated such that the sensor data accumulated in the controller 110 for the work machine is periodically output to an external memory (for example, a USB flash memory) and that data in the external memory is output to the computer 104 for the manufacturer.

Additionally, the present invention is not limited to the above-described embodiments but may include various modified examples without departing from the scope of the present invention. For example, the present invention is not limited to embodiments including all of the components described above but includes partially deleted embodiments. Additionally, a part of the configuration according to a certain embodiment can be added to or replaced with the configuration according to another embodiment.

Additionally, configurations related to the above-described controllers and computers and the functions and processing of the configurations may be partially or wholly implemented in hardware (for example, logic executing each function is designed in an integrated circuit). Additionally, the configurations related to the controllers and the computers may be a program (software) read and executed by a calculation processing device (for example, a CPU) to implement functions related to the configurations of the controllers and the computers. Data related to the program can be stored, for example, in a semiconductor memory (flash memory, SSD, or the like), a magnetic storage device (hard disk drive or the like), and a recording medium (magnetic disk, optical disk, or the like).

Additionally, in the above description of the embodiments, control lines and information lines interpreted to be necessary for the description are illustrated. However, not all control lines and information lines related to the products are illustrated. Actually, substantially all the components may be connected to each other.

DESCRIPTION OF REFERENCE CHARACTERS

101A: Sensor
102: Pieces of sensor data
104: Computer (server) for manufacturer
104b: Storage device (database)
110: Controller for work machine
111: Computer for service
112: Computer for administrator
113: Computer for analysis company
210: Storage device (RAM)
211: Abnormality determining section
212: Cause identifying section
213: Manual transmitting section
214: Inquiry matter transmitting section
215: Data receiving section
216: Oil analysis alerting section
301: Oil analysis request
303: Analysis results
304: Analysis diagnosis results
501: Hydraulic excavator

The invention claimed is:

1. An oil diagnosis system including a controller configured to diagnose a machine on a basis of sensor data about a viscosity, a density, and a dielectric constant of oil, the sensor data being acquired via an oil property sensor mounted in the machine, the sensor data being used to obtain, for each of the viscosity, density, and dielectric constant of the oil, a moving average obtained by sequentially determining time-series average values, an amount of change per unit time, and a difference of an amount of change between values at different sensing points in time, the controller comprising:

a storage section configured to store abnormality determination values for the moving average, the amount of change per unit time, and the difference of the amount of change between values at different sensing points in time, the abnormality determination values each being specified for a corresponding one of the viscosity, density, and dielectric constant of the oil;

an abnormality determining section configured to determine abnormality of the oil on a basis of the moving average, the amount of change per unit time, and the difference of the amount of change between values at different sensing points in time, determined from the sensor data, and the abnormality determination values stored in the storage device in association with the moving average, the amount of change per unit time, and the difference of the amount of change between values at different sensing points in time; and a cause identifying section configured to identify, when the abnormality determining section determines the abnormality, a cause of the abnormality of the oil on a basis of any of the moving average, the amount of change per unit time, and the difference of the amount of change between values at different sensing points in time that correspond to an oil property determined to be abnormal, the oil property being one of the viscosity, the density, and the dielectric constant; and a transmission section configured to transmit, to an external terminal, a result for the cause of the abnormality identified by the cause identifying section.

2. The oil diagnosis system according to claim 1, wherein the controller transmits, to the terminal, a coping manual for coping with the cause of the abnormality, along with a result of identification identified by the cause identifying section.

3. The oil diagnosis system according to claim 1, wherein the controller further comprises:

an inquiry matter transmitting section configured to transmit inquiry matters to the other terminal when the cause identifying section fails to identify the cause of the abnormality; and an data receiving section receiving answers from the terminal, and the cause identifying section identifies the cause of the abnormality of the oil on a basis of the answers to the inquiry matters received by the data receiving section, and any of the moving average, the amount of change per unit time, and the difference of the amount of change between values at different sensing points in time that correspond to an oil property determined to be abnormal, the oil property being one of the viscosity, the density, and the dielectric constant.

4. The oil diagnosis system according to claim 3, wherein the controller further comprises an oil analysis recommending section configured to recommend, to the terminal, a need for oil analysis involving oil extraction when the cause identifying section fails to identify the cause of the abnormality of the oil on the basis of the answers to the inquiry matters received by the data receiving section, and any of the moving average, the amount of change per unit time, and the difference of the amount of change between values at different sensing points in time that correspond to the oil property determined to be abnormal, the oil property being one of the viscosity, the density, and the dielectric constant.

5. The oil diagnosis system according to claim 1, wherein
for the data about the viscosity, an upper abnormality determination value larger than an initial value for the viscosity and a lower abnormality determination value smaller than the initial value for the viscosity are set as the abnormality determination values, and for the data about the density and the dielectric constant, upper abnormality determination values larger than initial values for the density and the dielectric constant are set as the abnormality determination values,
the cause identifying section determines the cause of the abnormality of the oil:
to be fuel contamination when the abnormality determining section determines the oil to be abnormal on a basis of the data about the viscosity determined from the sensor data being smaller than the lower abnormality determination value,
to be soot contamination in a case where the abnormality determining section determines the oil to be abnormal on a basis of the data about the viscosity determined from the sensor data being larger than the upper abnormality determination value and where the amount of change per unit time for the dielectric constant, the amount of change being determined from the sensor data, is larger than a first amount-of-change determination value for determining an increase in dielectric constant, and
to be metal powder contamination in a case where the abnormality determining section determines the oil to be abnormal on the basis of the data about the viscosity determined from the sensor data being larger than the upper abnormality determination value and where the amount of change per unit time for the dielectric constant determined from the sensor data is smaller than the first amount-of-change determination value.

6. The oil diagnosis system according to claim 1, wherein
for the data about the density, an upper abnormality determination value larger than an initial value for the density is set as the abnormality determination value, and
the cause identifying section determines the cause of the abnormality of the oil to be oil degradation when the abnormality determining section determines the oil to be abnormal on a basis of the data about the density determined from the sensor data being larger than the upper abnormality determination value.

7. The oil diagnosis system according to claim 1, wherein
for the data about the dielectric constant, an upper abnormality determination value larger than an initial value for the dielectric constant is set as the abnormality determination value, and
the cause identifying section determines the cause of the abnormality of the oil to be water contamination in a case where the abnormality determining section determines the oil to be abnormal on a basis of the data about the dielectric constant determined from the sensor data being larger than the upper abnormality determination value and where the difference of the amount of change between the dielectric constants at different sensing points in time, the amount of change being determined from the sensor data, is larger than a second amount-of-change determination value for determining a rapid increase in dielectric constant.

* * * * *